United States Patent [19]

Stone et al.

[11] Patent Number: 4,546,640
[45] Date of Patent: Oct. 15, 1985

[54] POSITIVE AIR GAS DETECTOR

[76] Inventors: Richard J. Stone, 3426 Covey Trail, Missouri City, Tex. 77459; Luther H. Dunegan, 4630 Bagpipe La., Houston, Tex. 77084; George E. Smith, 2115 S. Fountain Valley, Missouri City, Tex. 77459

[21] Appl. No.: 503,726

[22] Filed: Jun. 13, 1983

[51] Int. Cl.[4] .............................................. G01N 7/00
[52] U.S. Cl. ........................................... 73/19; 73/153
[58] Field of Search ............................ 73/19, 23, 153; 166/250, 252, 264, 265; 175/48

[56] References Cited

U.S. PATENT DOCUMENTS

| | | | |
|---|---|---|---|
| 2,745,282 | 5/1956 | Rochon | 73/19 |
| 3,422,674 | 1/1969 | Schroeter | 73/153 |
| 3,942,792 | 3/1976 | Topol | 73/19 |
| 4,310,058 | 1/1982 | Bourgoyne, Jr. | 175/48 |
| 4,319,482 | 3/1982 | Bunner | 73/153 |
| 4,330,385 | 5/1982 | Arthur et al. | 73/23 |

FOREIGN PATENT DOCUMENTS 2235724 1/1975 France ................................. 73/19

Primary Examiner—Stephen A. Kreitman
Attorney, Agent, or Firm—Vaden, Eickenroht, Thompson & Jamison

[57] ABSTRACT

Disclosed is an apparatus for continually monitoring for the presence of suspended or dissolved gas within a viscous material, such as in the material accumulated in the mud reservoir of a mud system used in an oil or gas drilling operation. Pressurized air is injected into the liquid to agitate and dislodge the gas. The dislodged gas is captured within a sealed chamber upon emerging from the liquid. A sample of the gas is continuously vented from the chamber through an outlet tube under the influence of the pressurized air. A gas sensor is mounted with the outlet tube so as to continually and accurately detect the presence of the gas within the liquid.

16 Claims, 3 Drawing Figures

POSITIVE AIR GAS DETECTOR

FIELD OF THE INVENTION

The present invention relates generally to a device for monitoring the presence of a gas and more particularly to releasing, sensing and measuring the amount of gas present in a heavy viscous fluid.

BACKGROUND OF THE INVENTION

Referring to FIG. 1, a schematic representation is shown of a well being drilled for the production of hydrocarbons. Generally, a drill string 10 with a drill bit 12 is employed as is shown in borehole 14. Drilling mud is circulated downwardly through the drill string, as shown by arrow 16. The mud circulates downwardly through the string, passes out through the drill bit and upwardly through the annulus surrounding the drill string, eventually exiting therefrom, as shown by arrow 18.

Drilling mud is employed in the drilling operation for many reasons. For example, mud provides lubrication for the cutting surfaces and promotes the cutting action. In addition, it carries heat away from the cutting surfaces, reducing wear, and carries the cuttings away so as to constantly expose a fresh earth part of the formation. However, one of the purposes of a drilling system is to provide weight to the formation above the point of drilling. This is a safety feature. Should a gas pocket be encountered, it will naturally try to push upwardly to escape. The mud prevents this from occurring as violently and dramatically as would otherwise be the case by providing a weight on top of the exposed formation including gas. Different mud compositions vary greatly; however, a common mud weight is 18 pounds per gallon.

When gas, usually methane gas, seeps into the borehole from the formation during drilling, a bubble of such gas exists in the borehole under a great deal of pressure, for instance 8,000–10,000 pounds per square inch. The gas bubble, of course, displaces a small amount or volume of mud, as shown at bubbles 20 in FIG. 1. The mud is heavy and viscous, but a bubble entering the borehole near the bottom will rise and as it rises at bubble 22, then bubble 24, then bubble 26, and finally at bubble 28, the bubble becomes larger and larger because not as much pressure is applied to the bubble at the top of the borehole as at the bottom. Hence, it may be evident, that when there is gas in the mud, some of the volume previously occupied by relatively heavy mud is occupied by the gas and the weight of the column is much reduced compared with gas-free mud. If allowed to continue, this process will accelerate, possibly to the point of an uncontrolled blowout resulting in loss of the well and extensive damage. Also, the presence of increasing gas in the mud is an indication, a warning as it were, of approaching a gas formation to which the drilling is directed.

In FIG. 2, there is shown a conventional apparatus used for detecting gas and drilling mud, including mud reservoir 50 to which drilling mud 52 is introduced through inlet 54 after being circulated through wellbore 14 as illustrated in FIG. 1. Suspended or dissolved within the drilling mud may be found various amounts of numerous gases as well as other products, to which the drilling mud was exposed during subsurface circulation. Typically, as mentioned above, the primary gas constituent part is methane gas although other gases, such as butane and isobutane, are frequently present as well. The drilling mud is extracted from reservoir 50 through outlet 56 as needed, to be cleaned of contaminants and reused.

In order to extract a sample of the gas suspended within the mud, container 58 is partially immersed within the drilling mud. Container 58 is open ended and is positioned to allow drilling mud 52 to partially fill interior 60 of the container. Mechanical agitator 62 is mounted with container 58 and includes rotatable shaft 64 extending downwardly into drilling mud 52. Propeller 66 is mounted on the shaft and is rotated within the drilling mud by power unit 68. Rotation of propeller 66 mechanically agitates the drilling mud, tending to dislodge dissolved or suspended gases therefrom. The gases, being less dense than the drilling mud, emerge from the surface thereof and continue to rise as at 69 under influence of subsequently emerging gas.

The gas eventually rises out of chamber 58 and encounters open framework 70 mounted on the container. The framework supports funnel or collector 72 positioned over the center of container 58. The gas flows into funnel 72, through conduit 74 and gas sensor 76 under the influence of vacuum pump 78 mounted with the conduit. The gas is then allowed to vent through outlet 80. Gas sensor 76 is responsive to the presence of gas flowing therethrough and produces an electrical signal which is transmitted over electrical connection 82 and displayed on meter 84. Frequently, gas sensor 76 is located remotely from reservoir 50 to enable monitoring activity to be accomplished at a distance or at a central control location.

As can be seen, the gas is exposed to environmental conditions after leaving interior 60 of container 58 and until entering funnel 72. Consequently, gas sensor 76 may not be able to measure the actual concentration of gas contained in the drilling mud. In recognition of this, gas sensor 76 is designed to measure fluctuations in the relative level of gas, not an absolute amount. That is, a sharp increase of gas detected in the sample is indicative of dangerous down hole conditions or possibly the presence of a hydrocarbon deposit, as previously discussed.

However, this conventional approach suffers from several inefficiencies and limitations. The gas sample may be diluted by breeze 86 prior to entering funnel 72, or by the dispersement of a portion of the gas to the atmosphere, as at 88. This prevents the gas sensor from reliably detecting variations in the amount of gas, since the measurement would not be more consistent than the force and direction of the breeze or other environmental conditions.

Additionally, a puncture anywhere along the length of conduit 74, even if of small dimensions, will be troublesome as the negative pressure existing therein will draw atmospheric gases into the sample stream to dilute the sample. Finally, dependence on a vacuum to gather and transport the gas sample is inefficient, in that methane and the other gases frequently encountered are heavier than air and resist mechanical efforts to force these heavier gases to flow upward until the influence of the vacuum pump takes over. Even then, these gases tend to "bunch", and produce irregular fluctuations in gas detector readings.

Therefore, it is a feature of the invention to provide an improved gas detector which measures the absolute quantity of the gas suspended or dissolved in a viscous liquid.

It is another feature of the invention to provide an improved gas detector which accurately senses variations in the level of gas suspended or dissolved in a viscous liquid.

It is yet another feature of the invention to provide an improved scheme to agitate and dislodge a gas dissolved or suspended in a viscous liquid by introducing pressurized air into the viscous liquid at a controlled rate.

It is still another feature of the invention to provide an improved scheme to utilize pressurized air to transport a gas sample from a sealed chamber to a remote gas sensor.

It is yet another feature of the invention to provide an improved method and apparatus for accurately measuring the absolute quantity of methane gas or the like dissolved or suspended in drilling mud circulated through a wellbore during drilling operations.

These and other objects, advantages and features of the invention will be apparent to those skilled in the art from consideration of the specification, including the attached drawing and appended claims.

SUMMARY OF THE INVENTION

The present invention includes a cylindrical container having one end closed and the opposite end open. The open end is inserted into a quantity of highly viscous material, such as drilling mud contained in a mud reservoir. The drilling mud is allowed to partially occupy the interior of the container, defining a sealed chamber in the unoccupied upper portion thereof.

Pressurized air is introduced into the drilling mud within the container at a controlled pressure and flow rate. The pressurized air tends to agitate and dislodge gas suspended or dissolved within the drilling mud. The dislodged gas and air flows upward and accumulates in the sealed chamber under pressurized conditions. A sample of the gas is continuously ejected exteriorally of the container through a vent connected to an outlet tube located above the drilling mud. The sample is exposed to a flowthrough sensor mounted with the outlet tube to measure the absolute quantity of gas. Alternatively, the flowthrough sensor may accurately measure fluctuations in the gas content of the drilling mud. An auxiliary vent may also be provided to bleed excess pressurized gas from within the sealed chamber to maintain a relatively constant buildup of air within the chamber, while establishing a slow outflow of the gas sample through the vent.

BRIEF DESCRIPTION OF THE DRAWINGS

So that the manner in which the above-recited features, advantages and objectives of the invention, as well as others which will become apparent, are attained and can be understood in detail, more particular description of the invention briefly summarized above may be had by reference to the embodiment thereof which is illustrated in the drawings, which drawings form a part of this specification. It is to be noted, however, that the appended drawings illustrate only a preferred embodiment of the invention and is therefore not to be considered limiting of its scope, for the invention may admit to other equally effective embodiments.

In the Drawings.

DETAILED DESCRIPTION OF THE INVENTION

Figure 1:
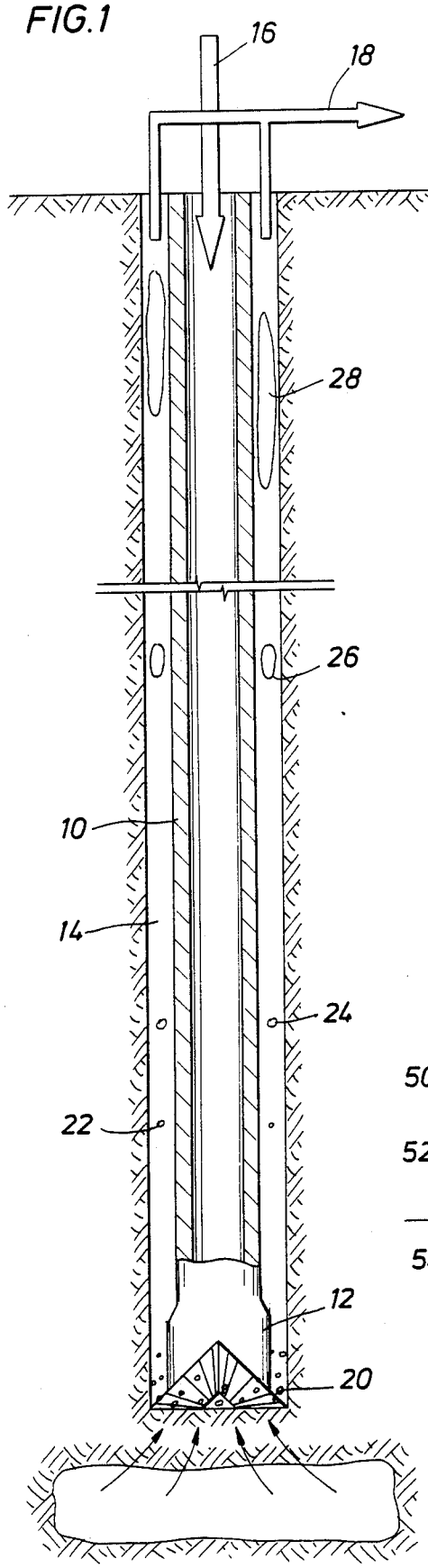
FIG. 1 is a schematic representation of an oil or gas well during drilling operations.
Figure 2:
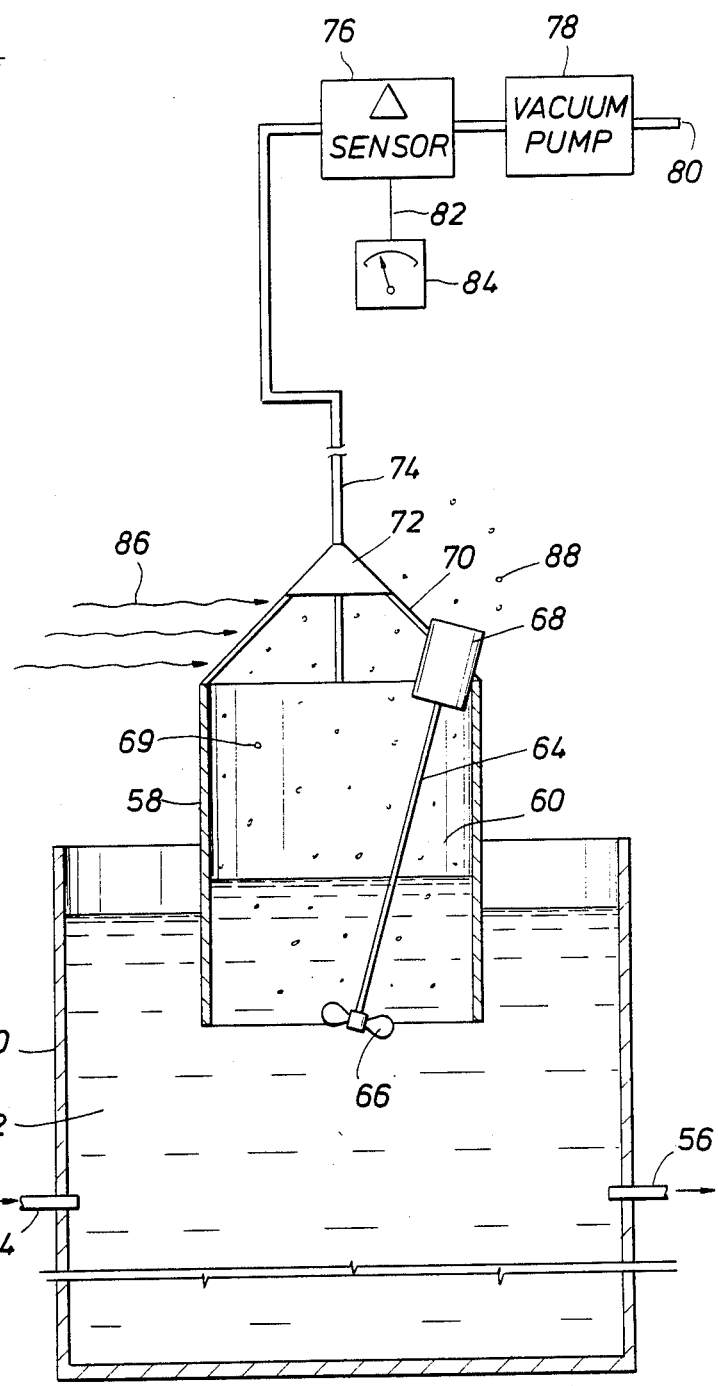
FIG. 2 is a schematic representation of a conventional gas detecting system.
Figure 3:
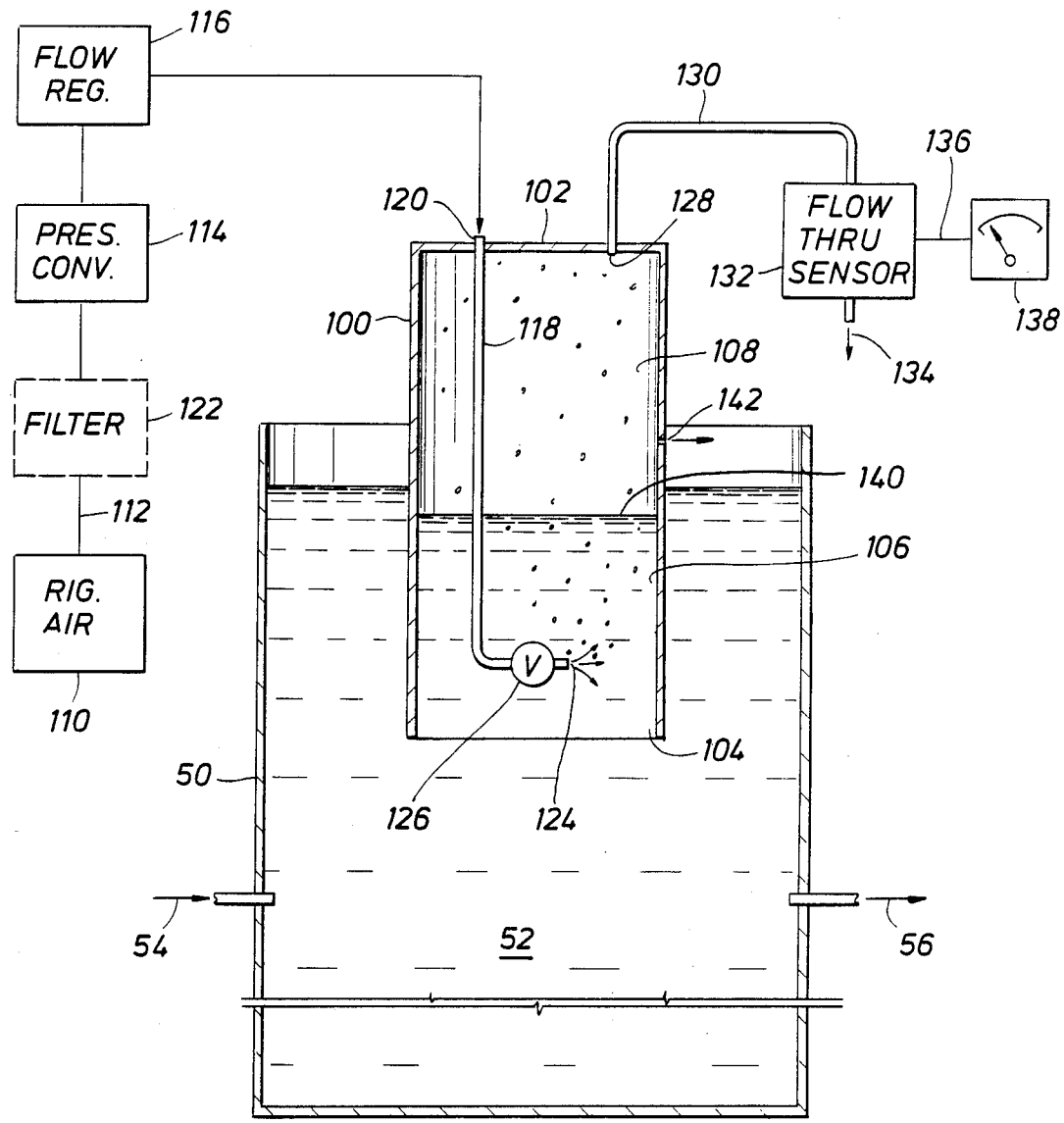
FIG. 3 is a schematic representation of a gas detecting system according to the present invention.

FIG. 3 shows mud reservoir 50 containing drilling mud 52 introduced through inlet 54 and extracted through outlet 56, as in FIG. 2. Chamber 100, having sealed end 102 and open end 104, is partially immersed in the reservoir, with open end 104 presented to the drilling mud so as to enable the mud to partially occupy interior 106 of container 100. Sealed chamber 108 is thereby defined within container 100 above the level of the mud contained therein.

Source of high pressure air 110 is located externally to the container. This source of pressurized air may conveniently take the form of an air compressor commonly found on drilling rigs providing air pressurized at approximately 120 pounds per square inch. The source of pressurized air is connected through conduit 112 to pressure converter 114, which may be used to reduce the pressure of the air to a level convenient to the process herein below described, such as 30 pounds per square inch. Conduit 112 likewise carries the pressurized air through flow regulator 116 which reduces the volumetric flow rate of the air to a level likewise found to be convenient, as will be explained in more detail later. Conduit 112 continues in like fashion to connect with inlet tube 118 through sealed end 102 of container 100 as at 120. It may be found convenient to include filter 122 within conduit 112 between source 110 and pressure converter 114 to remove particulate or other contaminants from the pressurized air stream which may interfere with the proper operation of the apparatus.

Inlet tube 118 extends into container 100 to a point below the mudline and enables injection of the pressurized air through spout 124 into the drilling mud. Backflow check valve 126 is provided within input tube 118. Check valve 126 is biased to a closed position, but may be maintained in an open position under the influence of a continuous stream of pressurized air. If the air is inadvertently cut off or if it is desired to discontinue the gas detection activity, the backflow check valve acts to prevent the entry of drilling mud 52 into inlet tube 118 where it may impair subsequent operation unless removed. The check valve may consist of a conventional spring biased ball valve and valve seat configuration, or alternatively, may comprise a flexible tube such as in U.S. Pat. No. 2,662,724, which collapses under the pressure of the drilling mud, yet is opened under the influence of pressurized air.

The injection of the pressurized air into the drilling mud produces three desirable effects. First, it produces a vigorous agitation of the drilling mud and dissolved or suspended gases. This agitation separates the gas from the mud adjacent the gas bubbles. Secondly, the dissolved gas has a greater tendancy to join the bubbles of pressurized air then return to suspension in the drilling mud. Since the mixture of air and gas is less dense than the drilling mud, the bubbles rise to the surface and enter the sealed chamber within the container. Thus, the air bubble acts as a vehicle for upward movement of the gases. The mixture within the sealed chamber will, over time, accurately reflect the composition of the gases within the drilling mud.

Thirdly, a continuous sample of the air/gas mixture in the chamber may be extracted through vent 128, sealingly connected to conduit 130. The sample is ejected through the vent under the influence of the pressurized air and is carried by conduit 130 to flowthrough gas meter 132 and outlet 134, whereafter the gas is released to the atmosphere or otherwise. Flowthrough gas meter 132 is constructed so as to measure the absolute quantity of gas in the sample. Because the sample has been isolated from the environment since emerging from the drilling mud, it is an accurate reflection of the composition of down hole conditions. This allows a precise and consistent measurement and hence, greater safety and control over the drilling operations.

The measurement by flowthrough meter 132 is converted to an electrical signal and carried by electrical connection 136 to meter 138, where it is displayed. Additionally, the signals may be monitored by an alarm (not shown) designed to be activated if the value of the gas content falls outside preselected limits. It is evident that flowthrough gas meter 132 or meter 138 may be positioned adjacent or remote from the reservoir, as desired. Of course, flowthrough gas meter 132 may be alternatively constructed to be responsive to fluxuations in gas content of the sample, as in previous devices. However, it will be evident that the operation of a gas detecting system sensitive to relative gas levels will be drastically improved as compared to previous devices due to the preservation of the integrity of the sample provided by the present invention.

Pressurized conditions within container 100 acts on the mud contained therein by lowering the surface level or mudline 140 within the chamber, compared to the remainder of the mud within reservoir 50 exposed to atmospheric pressure. This is just the opposite of conventional systems relying on mechanical agitation, as in FIG. 2, which tend to raise the level of the mud within the open-ended container, compared to the level of the mud in the remainder of the reservoir. The present invention provides a means for regulating the level of mud within the container so as to maintain mudline 140 above spout 124. As previously discussed, flow regulator 116 is provided within the conduit 112 to regulate the volumetric flow rate of the pressurized air. Under the pressure conditions described hereinabove, and for commonly encountered mud densities, the present invention may include a flow regulator designed to maintain a consistent volumetric flow of approximately 22 cubic feet per minute. Rather than allow the entire contents of chamber 108 to pass through vent 128, auxiliary vent 142 is provided to enable a controlled release or bleeding of the contents of the chamber. It has been found convenient to allow approximately 19 feet per minute to escape through auxiliary vent 142. Under conditions of equilibrium maintained by the flow regulator, this establishes a flow rate of approximately 3 cubic feet per minute through conduit 130 which is exposed to flowthrough sensor 132. This rate is adequate to transport sufficient quantities of gas to provide an accurate sample. Container 100 and inlet tube 118 may be constructed so that mudline 140 will never drop below spout 124 under the equilibrium conditions outlined above. The operation of the present invention is uneffected by punctures and leaks in conduit 130 as the higher than atmospheric pressure of the gas stream will not allow ambient gases to enter the conduit and dilute the sample.

From the foregoing, it will be seen that this invention is one well adapted to attain all of the ends and objects hereinabove set forth, together with other advantages that are obvious and that are inherent to the apparatus and structure. It will be understood that certain features and subcombinations are of utility and may be employed without reference to other features and subcombinations. This is contemplated by and is within the scope of the claims.

Because many possible embodiments of may be made thereof, it is to be understood that all matters herein set forth, and shown in the accompanying drawings, are to be interpreted as illustrative and not of a limiting sense, and equivalent structures will become apparent to those skilled in the art to which the invention pertains.

What is claimed is:

1. A gas detector apparatus for sensing the amount of gas present in a reservoir of heavy viscous material, comprising:

a container positioned with the reservoir, said container being open at the bottom and closed at the top, the walls of said container at the bottom being below the surface of the viscous material and apart from the bottom of the reservoir so that the material from the reservoir freely enters the container, the top of the container being above the surface to establish an air chamber above the surface of the reservoir material;

an input tube with a spout located within the container below the surface of the viscous material;

constant air pressure means connected to the inlet opening of said tube to cause air flow agitation of the viscous material within the container to dislodge residual gas therefrom whereby the gas and said compressed air rise and accululate in said air chamber at higher than atmospheric pressure; and an output tube connected to the air chamber through a first vent, whereby the pressurized gas and said air within within said air chamber are ejected through said vent and output tube; and a flow-through sensor connected downstream to said output tube for sensing gas present in the sample of air from the air chamber.

2. A gas detector apparatus in accordance with claim 1, wherein said flow-through sensor senses the abselute quantity of gas.

3. A gas detector apparatus in accordance with claim 2, and including a meter connected to said flow-through sensor for indicating the value of the gas sensed by said flow-through sensor.

4. A gas detector apparatus in accordance with claim 1, wherein said air chamber is vented to the environment through a second vent and the size of said second vent, the size of said output tube and said flowthrough sensor, and the air pressure established by said constant air pressure means cause a relatively constant pressure build up of air within said air chamber with at least a slight outflow of air therefrom through said first vent.

5. A gas detector apparatus in accordance with claim 1, wherein said constant air pressure means, comprises a pressure reduction converter connected to a source of high pressure of air, and a flow regulator connected to said pressure reduction converter for maintaining the volumetric flow rate to said input tube at a relatively constant level.

6. A gas detector apparatus in accordance with claim 5, wherein the output of said pressured reduction converter is at about 30 pounds per square inch.

7. A gas detector apparatus in accordance with claim 6, wherein the output from said pressure regulator maintains the volumetric flow rate of said air at approximately 22 cubic feet per hour.

8. A gas detector apparatus in accordance with claim 1, wherein said flow-through sensor senses the change of the quantity of gas.

9. A gas detector apparatus in accordance with claim 1, wherein the reservoir of heavy viscous material is a mud reservoir for a hydrocarbon drilling operation and the sensed gas is methane gas introduced into the mud from the earth formation during the drilling operation.

10. A gas detector apparatus in accordance with claim 1, wherein said input tube is terminated at its spout with a valve to prevent flow-back of the viscous material into said input tube in the event of temporary pressure drop in the flow of air from said input tube.

11. A method for detecting gas in a viscous liquid, the steps comprising:
  (a) injecting pressurized air into the viscous liquid to agitate the viscous liquid and dislodge the gas;
  (b) capturing the dislodged gas and said pressurized air within a sealed container as they emerge from the viscous liquid;
  (c) ejecting the gas out of said sealed container through a vent under the influence of said pressurized air; and
  (d) sensing the presence of the gas as it emerges from said vent.

12. A method for detecting gas suspended or dissolved in drilling mud contained in a mud reservoir after circulation through a wellbore during drilling operations, comprising the steps of:
  positioning a sealed container having an opening within the reservoir so that the drilling mud partially occupies the interior of said container and whereby the unoccupied portion of the container is isolated from atmospheric gases;
  injecting pressurized air into the drilling mud within said container;
  agitating the gas contained within the drilling mud with said pressurized air so as to dislodge the gas from the drilling mud;
  accumulating the gas and said pressurized air in the portion of said container interior not occupied by the drilling mud;
  ejecting the gas out of said container through a sealed outlet tube under the influence of said pressurized air; and
  exposing a gas sensor to the gas flowing through said outlet tube so as to detect the presence of gas within the drilling mud.

13. The method of claim 12, further including the steps of:
  regulating the volumetric flow of said pressurized air into said container; and
  bleeding said pressurized air from the portion of said container not occupied by the drilling mud in a controlled manner so as to maintain a relative equilibrium of pressure therewithin while establishing at least a slight outflow of gas through said outlet tube.

14. The method of claim 12, after the step of agitating and dislodging the gas, further comprising the step of:
  absorbing at least a portion of the dislodged gas in said pressurized air while rising through the drilling mud.

15. The method of claim 11, after step (a), the further step of:
  absorbing at least a portion of the dislodged gas in said pressurized air while rising within the viscous liquid.

16. A gas detector apparatus in accordance with claim 1, wherein said constant air pressure means comprises:
  a flow regulator connected to a source of pressurized air for maintaining the volumetric flow rate to said input tube at a relatively constant level.

* * * * *